United States Patent [19]

Pomerantz

[11] Patent Number: 5,081,158

[45] Date of Patent: * Jan. 14, 1992

[54] COMPOSITIONS AND IN SITU METHODS FOR FORMING FILMS ON BODY TISSUE

[75] Inventor: Edwin Pomerantz, Woodland Hills, Calif.

[73] Assignee: Zila Pharmaceuticals, Inc., Phoenix, Ariz.

[*] Notice: The portion of the term of this patent subsequent to Jan. 14, 2009 has been disclaimed.

[21] Appl. No.: 474,743

[22] PCT Filed: Jul. 24, 1989

[86] PCT No.: PCT/US89/03216

§ 371 Date: Mar. 8, 1990

§ 102(e) Date: Mar. 8, 1990

[87] PCT Pub. No.: WO90/01047

PCT Pub. Date: Feb. 8, 1990

Related U.S. Application Data

[63] Continuation-in-part of Ser. No. 189,032, May 2, 1988, abandoned.

[51] Int. Cl.$^5$ ............... C08L 1/26; A61K 9/08; A61K 31/60; A61K 31/69; A61K 31/72

[52] U.S. Cl. .................... 514/781; 106/189; 106/197.1; 514/57; 514/64; 514/159; 514/163; 514/925; 514/928; 514/969; 514/944

[58] Field of Search ............... 514/414, 781, 925, 928; 424/434, 435, 488

[56] References Cited

U.S. PATENT DOCUMENTS

| | | | |
|---|---|---|---|
| 4,226,848 | 10/1980 | Nagai et al. | 424/434 |
| 4,244,948 | 1/1981 | Boghosian et al. | 514/859 |
| 4,285,934 | 8/1981 | Tinnell | 514/934 |
| 4,292,299 | 9/1981 | Suzuki et al. | 424/434 |
| 4,381,296 | 4/1983 | Tinnell | 514/934 |
| 4,434,181 | 2/1984 | Marks et al. | 514/781 |
| 4,765,983 | 8/1988 | Takayanagi et al. | 424/434 |
| 4,767,612 | 8/1988 | Hagen et al. | 424/434 |
| 4,913,897 | 4/1990 | Chvapil et al. | 424/422 |

OTHER PUBLICATIONS

Herpaway, product description, Zila Pharmaceuticals, Inc., Las Vegas, Nev., NDC 0151-2844-67 prior to Jan. 1984.

Zilactin Medicated Gel, product description, Zila Pharmaceuticals, Inc., Phoenix, Az., 12004-893 first use: Aug. 17, 1987.

Zilactin Medicated Ointment, product description, Zila Pharmaceuticals, Inc., Phoenix, Az., NDC 51284-46-8-02 first use: Jan. 30, 1984.

*Primary Examiner*—Ronald W. Griffin
*Attorney, Agent, or Firm*—Fulwider, Patton, Lee & Utecht

[57] ABSTRACT

Medicated protective films are formed in situ on body tissue by applying a composition comprising (a) hydroxypropyl cellulose; (b) an esterification agent which reacts with the hydroxypropyl cellulose to form a reaction product which is soluble in the solvent of (c), but insoluble in body fluids at body temperatures; and (c) a nontoxic volatile solvent for said hydroxypropyl cellulose and said reaction products; and (d) a separate medicinal component. The films are tough, resilient and adhesive to body tissue including the mucosa.

5 Claims, No Drawings

COMPOSITIONS AND IN SITU METHODS FOR FORMING FILMS ON BODY TISSUE

This application is a continuation-in-part of my co-pending International Application PCT/US88/02515, filed July 25, 1988 which is, in turn, a continuation-in-part of my prior U.S. application Ser. No. 189,032, filed May 2, 1988, now abandoned.

This invention relates to compositions and methods for in situ treatment of body tissues.

In another respect, the invention pertains to the use of hydroxypropyl cellulose (HPC) in the manufacture of such compositions and the use of such compositions, manufactured from HPC.

According to another aspect, the invention relates to methods of treating skin, mucosal tissue and other moist tissue, by forming an adherent film thereon.

In another respect, the invention relates to compositions and methods for forming films in situ on body tissues, which films are effective sustained release carriers for medicinal and cosmetic components, to maintain such medicaments at and on a treatment site on body tissue.

In the topical treatment of body tissue, problems are encountered in maintaining treatment compositions in contact with the treatment site. The problem arises because normal movement of the treatment site and surrounding tissue, as well as abrasion or irrigation of the treatment site, causes topical compositions to be displaced.

In the case of mucosal tissue, it is considered practically impossible to maintain a treatment composition at the treatment site for more than a few minutes. The mucosal tissues are glaborous and initially wet which interferes with attempts to adhesively secure a treatment composition to these tissues.

The use of topical anesthetics for reducing pain is known. For example, commercially-available preparations containing benzocaine are widely used. However, these do not form coherent films in the mouth and are easily displaced from the ulcer site by saliva and physical movement of the surrounding tissues. An intra-oral ointment base for use in the oral cavity has been proposed which consists essentially of sodium carboxymethyl cellulose and pectin. However, such ointments are not considered sufficiently persistent to solve the basic problem of maintaining a topical analgesic agent in contact with an ulcer for up to several hours.

Topical adhesive dosages for mucosal ulcers have also been proposed in the form of a two-phase tablet having an adhesive peripheral layer of hydroxypropyl cellulose with the medication carried in an oleaginous core of cocoa butter. This device adheres to the mucosa of dogs for thirty minutes to six hours.

Mixtures of hydroxypropyl cellulose (HPC) and polyvinylacetate have been proposed as film-forming carriers for medications, but no use of such systems for intra-oral application of topical medicines has resulted.

Precast films of hydroxypropyl cellulose containing analgesics and antibiotics has been reported anecdotally for the treatment of pain of leukoplakia.

Alkyl cellulose and/or cellulose ether compounds have been used as thickeners or ointment bases for a wide variety of medicaments. For example, an alkyl cellulose, believed to be methyl cellulose, was used as a carrier and ointment base for the topical medicinal composition described in U.S. Pat. No. 4,381,296 to Tinnell.

Hydroxyethyl cellulose and/or hydroxypropyl cellulose was used to form a gel for application of the topical acne medications of U.S. Pat. No. 4,244,948 to Boghosian et al. And a water-soluble film formed of hydroxypropyl cellulose was used as the carrier for a bactericide in a teat-dip composition in U.S. Pat. No. 4,434,181 to Marks et al.

Heretofore it was understood that the relief of pain associated with recurrent aphthous stomatitis (RAS) ulcers was temporarily alleviated by the medicinal composition of Tinnell '296 patent in an alcohol-methlcellulose carrier. However, more recently, it has been demonstrated that a principal analgesic effect is due to a protective film which forms, which acts as a barrier to further insults of the ulcer by foods, saliva, etc. Moreover, it is now understood that the barrier film formation is due to chemical reaction of the medicinal compositions of Tinnell '296 and the cellulosic thickener, rather than by simple deposition of the cellulosic material per se, upon vaporization of the alcoholic solvent. Further, it has now been discovered that the cellulosic component of the commercially available gels containing the Tinnell '296 medicaments is, in fact, hydroxypropyl cellulose, rather than methylcellulose as previously understood, Finally, I have determined that the mechanism of film formation is specific to hydroxypropyl cellulose. Closely related alkyl or hydroxyalkyl-substituted cellulose, such as methylcellulose, hydroxyethyl cellulose and hydroxybutyl cellulose are not suitable substitutes for HPC.

The barrier effect of the film derived from HPC provides practically instantaneous and long-lasting substantial reduction of the pain associated with aphthous and other ulcers and trauma. This pain relief and prevention activity by the barrier action of the film is very surprising in view of the previous belief that is was necessary to provide an analgesic, e.g., benzocaine, at the ulcer site.

I have further discovered that the compositions for forming the HPC-derived films in situ on body tissues can also function as stable carriers for a wide variety of medicinal components. When such compositions are applied as a treatment to body tissue, the medicinal components are incorporated in the resulting in situ formed films, from which they are released to provide a sustained supply of the medicine at the treatment site.

Briefly, in accordance with my invention, I use HPC in the manufacture of a film-forming composition for topical treatment of human tissue. The composition comprises hydroxypropyl cellulose, an esterification agent, and a suitable volatile solvent which functions as a medium for reaction of the HPC and the acid and also to maintain the esterification reaction product in the form of a gel or lotion for convenient application. Such compositions are especially adapted to treatment of trauma of skin and mucosal tissue from external causes, e.g. cuts, abrasions, incisions and burns, as well as bacterial and fungal infections and ulcers of unknown etiology.

Advantageously, the solvent is alcoholic, e.g. ethyl, isopropyl or methyl alcohol. The specific solvent is chosen for its ability to dissolve the HPC and esterification agent and to maintain the esterification reaction product in solution or suspension until application of the composition to the treatment site. Obviously, the solvent should not be toxic to the body in the quantities employed.

The esterification agent can, advantageously, be a weak carboxylic acid which is substantially non-toxic. The specific acid or acids are selected for their ability to react with the HPC to form an esterification reaction product (see below) which is soluble in the reaction mixture at storage temperatures, e.g. 40-80 degrees Fahrenheit, but which is insoluble in body fluids at or near body temperatures and above. Suitable weak organic acids include salicylic acid and tannic acid and mixtures thereof. Other suitable esterification agents can be identified by those skilled in the art, having regard for this disclosure.

According to another embodiment of the invention, I provide compositions which comprise the film-forming compositions described above and a biologically active topical treatment component, cosmetics, or medication. The biologically active component is physically incorporated in the film-forming components and in the films formed therefrom, to provide medically effective quantities of the topical agent at the treatment site on body tissue. The incorporated biologically active components are thus maintained in contact with the tissue for a time effective to treat the medical condition for which they are intended, rather than being displaced by physical movement of the tissue, abrasion or by irrigation by body fluids. There are indications that the films provide a sustained release mechanism which increases the efficacy of the treatment. The HPC derived films are inert and do not interfere with the normal action of the topical treatment agent.

According to my present understanding, the esterification component of the compositions esterifies at least a portion of the HPC. This esterification reaction apparently takes place primarily upon drying of the solvent carrier. The HPC and acid components of my composition, as well as any ester derivative which may form in solution prior to application of the composition to the body tissue are soluble in the solvent carrier at room temperature under normal pre-application and storage conditions. However, upon application of the compositions and air-drying of the solvent, with further esterification, a film is formed in situ which is insoluble in body fluids at and above normal body temperature of about 37 degrees centigrade.

In a presently preferred embodiment of the invention, I also incorporate a non-toxic weak cross-linking agent in the compositions of the invention. The resultant in situ formed film is somewhat tougher and more resilient and has better adhesion to body tissue than such films which are formed from compositions without such cross-linking agent. The agents for cellulosic compounds, the specific agent being chosen so as to avoid premature formation of an insoluble mass prior to application of the composition. According to present knowledge, boric acid is an appropriately effective cross-linking agent for use in practicing the present invention. While I do not wish to be bound by this mechanism, it appears that the cross-linking agent effectively bonds some of the unesterified hydroxyl groups into the film formed on drying of the composition after application to the body issue. This belief is based on the observation that without a cross-linking agent in the composition, two film layers may actually form upon drying of the solvent, one of which is believed to be a film of the esterified HPC and the other of which is a less tenacious film of un-esterified HPC. Presence of the cross-linking agent apparently bonds these two film layers resulting in a more tenacious, tough and durable film formed in situ on the body tissue.

The HPC-derived films are soluble in ethyl alcohol and similar non-toxic volatile solvents, e.g., isopropyl alcohol and the like, but are insoluble in water and water-containing body fluids, e.g., saliva at normal human body temperature. Films formed by evaporation of the solutions are tough, resilient and adhesive to body tissues and form a protective barrier against air, other body fluids and foreign substances.

The cellulosic compound, which is reacted with weak carboxylic acids to form the film according to my invention, is selected for its ability to react with the carboxylic acid component to form a film which is insoluble in water and aqueous body fluids at a temperature equal to or greater than body temperature. According to present knowledge, hydroxypropyl cellulose (HPC) is suitable. Such cellulosic compound is available commerically, for example, the product sold under the name "Klucel", a registered trademark of Aqualon Company. The type "MF" Klucel product is particularly suitable.

The solvent for forming the solutions of the HPC is selected for its ability to dissolve the HPC and HPC esters and its non-toxic characteristics when the composition is applied in the amount necessary to from a protective film. For example, ethyl alcohol is preferred when the film is to be deposited in the oral cavity whereas isopropyl alcohol is suitable for use in depositing films on the skin. Other suitable solvents will be readily identified by those skilled in the art having a regard for he disclosures herein, e.g., volatile polar solvents which are medically compatible with body tissue.

The specific esterification agent component of the compositions is chosen for its ability to react with the HPC to form, upon air-drying of the composition, a tough resilient film which adheres to body tissue. Strong carboxylic acids, e.g., acetic acid, citric acid and the like do not provide this result. However, weak carboxylic acids, especially salicylic acid, tannic acid and the like and mixture thereof function effectively. The in situ film formation capability appears to be related to the solubility of the HPC derivative in water and aqueous body fluids at body temperature. Hence, any such weak carboxylic acid which is non-toxic and has the capability to form such insoluble films can be effectively employed, the selection of such weak acid being within the capability of persons skilled in this art, having regard for this disclosure. Salicylic acid and tannic acid have been identified as particularly effective in the practice of my invention. In fact, it now appears that a mixture of these two acids in the film forming compositions of the invention produce a superior film in terms of adhesion and mechanical integrity, although either of these acids alone provides an effective in situ deposited film.

The film of HPC which is formed by evaporation of the compositions is apparently a "physical film", i.e., the cellulosic compounds do not polymerize. Evidence of the physical characteristics of these films is provided by the fact that such film, once formed, simply re-dissolves upon further application of the compositions to the same site.

The film forming composition can be applied to the body tissue by any convenient technique, e.g., spraying, dipping or simple direct application by a swab.

According to the presently preferred embodiments of the invention, the HPC component is present in the solution in an amount from about 0.1-20% by weight of the final composition. The proportion of the HPC in the composition affects the time required for the composition to air dry and form the tough adhesive film. At lower contents of the HPC compound, the composition dries more slowly, but he resultant film is more coherent and abrasion-resisitant. At higher contents, the film forms more quickly by air drying, but the resultant film is less coherent and adhesive owing to the fact that the portion of the film at the surface of the applied composition and at the body tissue surface dries at different rates.

At present, I prefer to employ some 0.1-10% by weight of HPC in the final composition, which provides an easily-applied gel, as distinct from a runny liquid. Best results are obtained with about 2.5% by weight of HPC in the gel composition. The carboxylic acid component of the composition can be a single acid, alone or in combination with other weak carboxylic acids. Whether present alone or in combination, however, the proportion of the carboxylic acid can vary from about 1 to about 10% by weight of the composition with the optimum concentration being closer to the upper portion of this range. Indeed, there are indications that higher proportions of the carboxylic acids do not appreciably interfere with the film formation. In the lower range, the film forms more slowly and is less coherent.

The compositions are applied typically in localized areas, to the body tissue and air-dried to form the film in situ, adhesively secured to the tissue. For best results, when applied to wet or moist tissue, steps should be taken to remove as much of the water, moisture or other body fluids from the surface of the body tissue before applying the composition. For example, when applied inside the mouth, normal dental procedures for substantially drying the mucosal tissue are employed and air is drawn or blown over the surface of the applied composition to promote more rapid evaporation of the solvent and formation of the film.

The compositions have been found especially useful in the treatment of aphthous ulcers of the mucosa, including recurrent aphthous stomatitis. This treatment provides essentially immediate and long-lasting relief of the exquisite pain associated with such ulcers in the formative and prelocalizing steps. The particular composition which has been found most effective in alleviating such pain, includes HPC, ethyl alcohol solvent, a mixture of tannic and salicylic acids as the weak carboxylic acid component and boric acid as the cross-linking agent. The composition is applied directly to the surface of the ulcer and surrounding mucosa with a swab and is air dried by simply ensuring that the patient breathes normally through the mouth. The film is adhesively retained on the ulcer site and surrounding mucosal tissue for extended periods of time, upwards of several hours. Furthermore, the initial pain relief, obtained by the exclusion of air, saliva, etc., from the ulcer, continues during this extended retension period and even prevents recurrence of the pain despite repeated attempts to cause pain onset by deliberately insulting the ulcer with irritating foods such as orange juice.

EXAMPLE 1

A composition is prepared by mixing the following components in the indicated proportions:

| Components | % (wt) |
| --- | --- |
| ethyl alcohol | 87 |
| hydroxypropyl cellulose | 2.5 |
| tannic acid | 7.0 |
| salicylic acid | 2.5 |
| boric acid | 1.0 |

EXAMPLE 2

The composition of Example 1 is tested for pain reduction capability in comparison with the commerically available medication sold under the name "Orabase", a composition containing benzocaine in a sodium carboxymethyl cellulose and pectin base.

Twenty otherwise healthy human subjects who suffer from recurrent aphthous stomatitis are separated into test and control groups of ten members each.

Comparable test sites consisting of an aphthous ulcer and surrounding healthy mucosal tissue is selected in the mouths of each of the subjects. These sites are prepared by irrigating with distilled water and then carefully drying with cotton gauze pads.

The composition prepared according to this example is applied as a thin coating to the prepared aphthous ulcer sites in the mouths of the test group and a similar thin coating of the Orbase control medication is applied to aphthous ulcer sites in the mouths of the control group.

The patients of both the test group and the control group are required to breathe normally through the mouth for a period of two minutes, after which point it is noted that the composition of Example 1 has dried in the mouths of the test group patients to form a film over the aphthous ulcer site.

Observation of the test and control patients demonstrates that the films of the test composition are still present in place in 80% of the test subjects' mouths two hours after application, whereas the control medication completely disappears from the ulcer sites in all subjects in the control group.

EXAMPLE 3

The procedure of Example 2 is repeated except that, just prior to the preparation of the ulcer sites, the aphthous ulcers in the mouths of both the test and control patients are insulted by application of orange juice. The incidence of pain is clinically observed for a period of one hour, at which time the treated ulcer sites are once again insulted with orange juice. Pain observation is continued for an additional three hours.

In both the test and control groups, all patients experience a large increase in pain after the first insult, followed by a mild to significant decrease in pain after the immediate application of both the test and control compositions.

At the second insult, the patients in the test group which are treated with the composition of the present invention experience no increase in pain and continue to experience mild to substantial pain reduction for the succeeding three hours. However, the patients in the control group experience a large increase in pain at the second insult which decreases only slightly during the ensuing three hours.

EXAMPLE 4

The procedures of Examples 1-2 are repeated except that the compositions contain, respectively, 10% tannic acid, 10% salicylic acid and 7% boric acid. Both of these compositions yield comparable results to those set forth in Examples 2 and 3.

EXAMPLE 5

The boric acid cross-linking agent is omitted from the compositions of the preceeding Examples. The in situ deposited films formed from these compositions actually comprise two layers which can be mechanically separated. Although these two-layer films are effective in pain treatment, they are less persistent.

EXAMPLE 6

Therapeutically effective quantities of various topical medicines are incorporated into the compositions of Example 1. The resulting mixtures are shelf-stable and are topically applied to body tissue and air-dried, forming resilient adherent films containing the medicaments, which migrate to the treatment site to effectively accomplish the desired treatment.

Anesthetics

Benzocaine
Dycloninc hydrochloride
Hexylcaine hydrochloride
Pramoxine hydrochloride
Butamben picrate
Tetracaine hydroiodide

Anti-Inflammatory Agents

Hydrocortisone
Betamethasone valerate
Triamcinolone acetonide
Fluocinonide
Dexamethasone
Methylprednisone acetate

Antibiotics

Clindamycin
Erythromycin
Meclocycline sulfosalicylate
Tetracycline
Cholohexidine
Neomycin
Polymixin B sulfate
Bacitracin
Sulfadizine

Antifungal Agents

Clotrimazole
Miconazole
Nystatin
Acyclovis
Interferon
Vidasabine
Betadine

Miscellaneous Topical Agents

Salicylic acid
Isotretinoin
Aloe Vera
Alclomethazone dipropionate
Caprylic acid
Lindane
P.A.B.A.
Interferon
Aluminum Chorhydrate

EXAMPLE 7

The method for measuring percutaneous absorption of topical medications, described by McKenzie & Stoughton in *Arch. Dermatol* 1962; 86: 608-610 and, more recently in *Arch. Dermatol* 1985; 121: 63-67, was used to assess the clinical effectiveness of various topical medicaments incorporated into the film forming compositions of Example 1.

According to this method, the flexural aspect of a subject's forearms are cleansed and approximately 10 mg of the test material is applied to a clearly marked 8 $cm^2$ area. Four formulations are evaluated on four different 8 $cm^2$ areas on each arm, totaling eight formulations per subject. The formulations are applied at 4 p.m. and allowed to remain in place overnight. At 8 a.m. the test sites are gently washed with soap and water and read two hours after washing. The intensity of blanching is determined on a four-point scale. Twenty subjects were used to evaluate a panel of eight forumlations, with a ventilated guard placed over the test sites and ten subjects were used to evaluate the formulations with no guard placed over the test sites. The formulations tested were:

Formulation of EXAMPLE 1, plus 1. 1% hydrocortisone
2. 0.5% hydrocortisone
3. 0.05% betamethasone dipropionate
4. 0.1% triamainolone acetonide

Commercial Cream Formulations

5. Aristocort 0.1%
6. Kenalog 0.1%
7. Hytone 1.0%
8. Hytone 0.5%

The 4-point scale utilized is:

No blanching = 0
Mild blanching = 1
Moderate blanching = 2
Intense blancing = 3

The subject's test scores for each formulation were summarized to give a total score for that formulation.

A comparison of the scores for each formulation showed that, in all cases the formulations 1,2,3, and 4 provided essentially the same skin penetration of the active medicament, with and without the guard. Further, in the case of formulations 5 and 6 the total scores were less than half in subjects without guards than those with guards. In the case of formulations 7 and 8 the total scores with and without guards were approximately equal, but also approximately equal to formulations 1 and 2 with no guard.

These results demonstrated that the in situ films containing the active ingredients (Examples 1-4) were persistent and resisted displacement by abrasion, rubbing, etc., overnight and that the active medicaments therein were effectively transferred to the underlying tissue.

EXAMPLE 8

The ability of the film forming compositions of Example 1 to carry and effectively release antibiotics was demonstrated by incorporating 1% neomycin therein. This formulation was compared to a commerical 1% neomycin cream by applying the formulations to hairless mouse skins (10 replications) and agar plates (4 replications) inoculated with staph. aureus. The radio of inhibitions (mm) of each replicate were summed to give a total score for each formulation. The results were:

| Plate | Mouse Skin | Agur |
|---|---|---|
| Film forming composition of Example 1 plus 1.0% Neomycin | 11 | 49 |
| Commerical 1% Neomycin Cream | 7 | 47 |

Having described my invention in such terms as to enable thoses skilled in the art to understand and practice it, and having described the presently preferred embodiments thereof,

I claim:

1. A liquid composition for in situ formation of medicament films on body tissue, comprising:

(a) 0.1 to 20 percent by weight of hydroxypropyl cellulose;
   (b) an esterification agent which reacts with the hydroxypropyl cellulose to form a reaction product which is soluble in the solvent of paragraph (c), but insoluble in body fluids at body temperatures;
   (c) a nontoxic volatile solvent for said hydroxypropyl cellulose and said reaction product; and
   (d) a separate medicinal component in addition to said esterification agent.

2. The composition of claim 1 wherein the esterification agent is a weak organic acid.

3. The composition of claim 2 in which the esterification agent is salicylic acid.

4. The composition of claim 2 in which the esterification agent is a mixture of salicylic and tannic acid.

5. The composition of claim 4 in which the esterification agent further includes boric acid as a cross-linking agent.

* * * * *